United States Patent [19]
Ahlstrom et al.

[11] Patent Number: 5,433,116
[45] Date of Patent: Jul. 18, 1995

[54] APPARATUS FOR MEASURING PREVAILING INSTANTANEOUS TENSION IN AN ELONGATE STRAND

[75] Inventors: Kevin S. Ahlstrom; Thomas Bartlett, both of Waxhaw, N.C.

[73] Assignee: On Line, Inc., Waxhaw, N.C.

[21] Appl. No.: 201,171

[22] Filed: Feb. 24, 1994

[51] Int. Cl.⁶ .............................................. G01N 3/08
[52] U.S. Cl. ...................................... 73/828; 73/160; 73/829; 73/862.474
[58] Field of Search ................... 73/828, 160, 829, 849

[56] References Cited

U.S. PATENT DOCUMENTS

| | | | |
|---|---|---|---|
| Re. 31,312 | 7/1983 | Eddens | 73/862.48 |
| 3,140,604 | 7/1964 | Bernet | 73/160 |
| 3,141,329 | 7/1964 | Canning | 73/160 |
| 3,183,711 | 5/1965 | Duncan | 73/828 |
| 3,229,175 | 1/1966 | Strandberg | 318/6 |
| 3,274,824 | 9/1966 | Lawson et al. | 73/829 |
| 3,327,525 | 6/1967 | Russell et al. | 73/849 |
| 3,376,740 | 4/1968 | Harvey | 73/862.474 |
| 4,064,744 | 12/1977 | Kistler | 73/849 |
| 4,078,231 | 3/1978 | Artzt et al. | 340/259 |
| 4,213,056 | 7/1980 | Matsumura et al. | 250/559 |
| 4,295,360 | 10/1981 | Fountain | 73/15.6 |
| 4,346,601 | 8/1982 | France | 73/829 |
| 4,584,875 | 4/1986 | Woo et al. | 73/160 |

FOREIGN PATENT DOCUMENTS

| | | | |
|---|---|---|---|
| 0148337 | 7/1986 | Japan | 73/849 |
| 0848489 | 7/1981 | U.S.S.R. | 73/828 |

OTHER PUBLICATIONS

Brochure "EMS Ellipsoid Mini Sensor", HBM, Inc., undated, 2 pages.

Primary Examiner—Richard E. Chilcot, Jr.
Assistant Examiner—James M. Olsen
Attorney, Agent, or Firm—Shefte, Pinckney & Sawyer

[57] ABSTRACT

The prevailing tension in an elongate strand, such as a textile yarn, is instantaneously measured, even at very low levels of tension and at fine incremental changes in tension, by a tension measuring apparatus utilizing a pair of fixed contact arms spaced from one another to define a strand contact line therebetween and an intermediate cantilevered sensing arm disposed at an equal spacing from each fixed contact arm and at a lateral spacing from the stand contact line. The fixed contact arms and the sensing arm are contacted with the strand simultaneously at the same common lateral side of the strand to cause the strand to deflect from the strand contact line at equivalent strand break angles between the respective strand contact points on the fixed contact arms and on the sensing arm. An electrically powered strain gauge, preferably incorporating a Wheatstone bridge circuit, is associated with the sensing arm to generate a continuous electrical output signal varying instantaneously in proportion to the corresponding instantaneous tension prevailing in the strand while in contact with the fixed contact arms and the sensing arm. In one embodiment, the measuring apparatus is contained within a portable hand-held housing for manual placement in contact with a strand whose tension is to be measured, with an auxiliary hand-held housing supplying electrical power to the strain gauge and containing a microprocessor to compute a quantitative tension value from the output signal received from the strain gauge.

22 Claims, 5 Drawing Sheets

APPARATUS FOR MEASURING PREVAILING INSTANTANEOUS TENSION IN AN ELONGATE STRAND

BACKGROUND OF THE INVENTION

The present invention relates generally to tension measuring devices and apparatus and, more particularly, to such apparatus for measuring the prevailing tension in an elongate strand.

Various industrial operations in diverse industries involve the handling of strand material and, particularly, the transportation of such material from one operational location to another. As used herein, the terms "strand" and "strand material" are intended to broadly encompass substantially any material of an elongate indeterminant length such as, by way of illustration but without limitation, yarns, threads, filaments, ropes, wires, cables, tapes, ribbons, and like materials.

In many cases, the control of the lengthwise tensioning of the strand material may be important and even critical to the effective accomplishment of an industrial operation. For example, in the textile industry, the handling of textile yarns, filaments and threads during various stages of differing textile manufacturing operations can be critical to controlling uniformity in the strand material itself, the processing thereof, and the resultant quality of textile fabric and other goods produced from the strand material.

As a result, various devices are employed in the textile and other industries for regulating the tension in strand material during handling and other devices are utilized for quantitatively measuring strand tension to verify accomplishment of the desired tension control.

As technology has progressed, certain strand materials used in the textile and other industries have become increasingly fine and delicate, necessitating careful handling at heretofore unconventionally low tension levels. Disadvantageously, conventional tension measuring devices are characteristically ill-equipped to detect accurately the prevailing tension level in a strand within low ranges of tension, e.g., less than one gram of tension.

SUMMARY OF THE INVENTION

It is accordingly an objection of the present invention to provide a novel apparatus capable of measuring prevailing instantaneous tension in an elongate strand at extremely low levels of tension, while also being well-suited for performing tension measurements in higher, more conventional ranges of strand tension.

Briefly summarized, the apparatus of the present invention accomplishes this objective by utilizing a pair of fixed contact arms in conjunction with a deflectable cantilevered sensing arm disposed therebetween and associated with an electrically-powered strain gauge device. More specifically, the fixed contact arms of the present apparatus are arranged at a spacing from one another wherein the fixed arms define a strand contact line therebetween for simultaneously contacting the strand in-situ at a common lateral side of the strand at respective points along the strand contact line. The cantilevered sensing arm is supported between the fixed contact arms at an equal spacing from each thereof and at a lateral spacing from the strand contact line for contacting the strand simultaneously with the fixed contact arms at a sensing point at the same common lateral side of the strand to cause the strand to deflect from the strand contact line at equivalent strand break angles between the respective strand contact points on the fixed contact arms and the sensing point on the sensing arm. The strain gauge device is associated with the sensing arm for generating a continuous electrical output signal varying instantaneously in proportion to the corresponding instantaneous tension prevailing in the strand in contact with the fixed contact arms and the sensing arm.

To achieve a desired degree of sensitivity in the deflectability of the cantilevered sensing arm, the sensing arm is provided with an opening laterally through the arm for reducing the force required to deflect the sensing arm from a resting cantilevered position. Preferably, the opening is of an ellipsoidal shape in relation to the length of the sensing arm to optimize the desired level of sensitivity.

The strain gauge device preferably is in the form of a Wheatstone bridge circuit having an excitation contact and a signal contact at each of two opposite sides of the sensing arm relative to a plane of deflection normal to the strand contact line for producing the electrical output signal in proportion to both strand tension increases and decreases.

The strain gauge device is preferably connected to a microprocessor or similar device adapted to be programmed for computing a quantitative tension value from the output signal of the strain gauge device and a display device is preferably associated with the processor for displaying the tension value computed thereby. In the preferred embodiment, the processor continuously computes the tension value instantaneously from the output signal and the display device continuously displays the instantaneously-computed tension value.

In one preferred embodiment, the apparatus of the present invention is constructed to be easily portable by a user from one strand tension-sensing location to another. More specifically, a first portable housing adapted to be held in one hand of a user supports the fixed contact arms, the sensing arm and the strain gauge device, while a second portable housing adapted to be held in the other hand of the user supports the processor or other computing device and the display device along with a suitable source of electrical power supply, e.g., a battery. Electrical leads extend through a sheath or cable between the two housings for connecting the strain gauge device with the electrical supply source, the processor and the display.

DESCRIPTION OF THE PREFERRED EMBODIMENT

Figure 1:
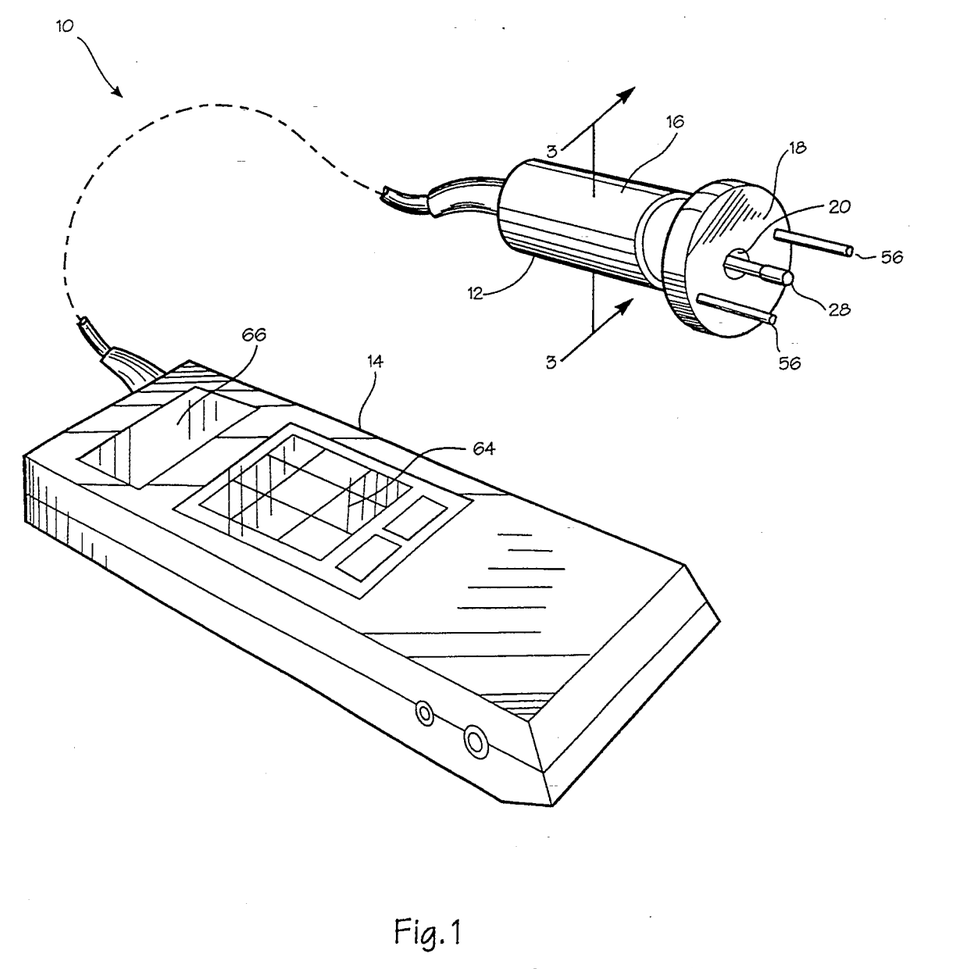
FIG. 1 is a schematic perspective view of one preferred embodiment of the strand tension measuring apparatus of the present invention, adapted for portable use.

Referring now to the accompanying drawings and initially to FIG. 1, the strand tension measuring apparatus is shown generally at 10 in one preferred embodiment adapted to be hand-held and readily carried by a user for easy portability from one strand tension-measuring location to another. However, of course, those persons of skill in the relevant art will readily recognize and understand from the disclosure of the invention set forth herein that the tension-measuring apparatus of the present invention is equally adaptable to applications wherein the apparatus would be mounted in a fixed location in a strand-handling system for continuous or intermittent operation as desired. Thus, it is to be understood that the description of the present invention herein set forth is provided by way of illustration of an exemplary embodiment for purposes of providing an enabling disclosure to persons skilled in the art, and the present invention is not to be limited to the described embodiment.

The tension-measuring apparatus 10 basically includes a first hand-held housing 12 adapted to be manually situated in contact with a strand whose tension is to be measured, as will be described more fully hereinafter, and a second hand-held housing 14 which provides operational power to the components within the housing 12 and receives, analyzes and displays tension-reflective signals from the housing 12. A cable 15 extending between and connecting the housings 12,14, encloses operational electrical leads as more fully described hereinafter.

With reference to FIGS. 1, 2A, 2B and 3, the housing 12 has a cylindrical shell 16 terminating at its forward end in a circular disk-like face 18 extending radially from the shell 16 and having a central opening 20 formed in the face 18 coaxial with the cylindrical shell 16. The opposite end of the cylindrical shell 16 is closed by a radial wall 22 to which one end of a moment arm assembly 24 is mounted to extend in cantilevered fashion axially through the cylindrical shell 18 and outwardly through the opening 20 in the circular disk 18. The moment arm assembly 24 includes a main body 26 of a rectangularly parallelpiped configuration, one end of which is affixed to the radial wall 22 of the cylindrical shell 16 and the opposite free end of which has affixed thereto a substantially cylindrical, slightly tapered strand contact arm 28 extending outwardly from the shell 16 through the opening 20.

As thusly mounted, the moment arm assembly 24 is deflectable in a plane P (FIG. 2A) and the parallelpiped main body 26 of the moment arm assembly 24 is oriented with opposed upper and lower surfaces 26′ 26″ oriented perpendicularly to the plane of deflection P and with the lateral side surfaces 26‴ oriented parallel to the plane of deflection P. To render the main body 26 more easily deflectable and thereby to enhance the sensitivity of the moment arm assembly 24 to deflecting forces, the main body 26 is formed with an opening 27 extending laterally therethrough between the opposed side surfaces 26″ the opening 27 preferably being of an ellipsoidal shape, as best seen in FIG. 3, so that the degree of deflection of the moment arm assembly 24 will be uniform for a given deflecting force regardless of the location at which the deflecting force is applied along the length of the strand contact arm 28.

Figure 6:
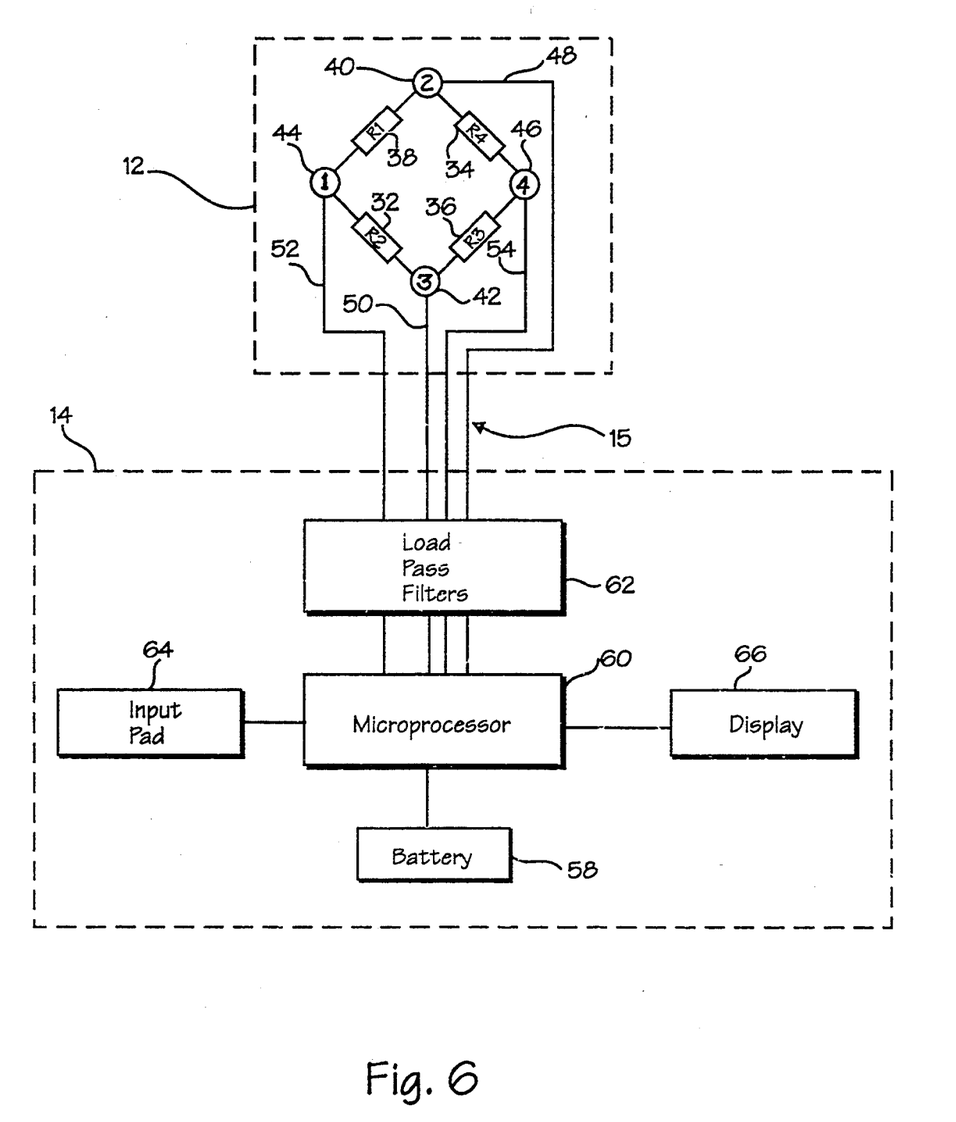
FIG. 6 is a schematic diagram relationally depicting the operational components of the two housings of the apparatus of FIG. 1.

A strain gauge device, generally indicated at 30 (see also FIG. 6), is mounted to the main body 26 of the moment arm assembly 24 for detecting and measuring deflections of the moment arm assembly 24. The strain gauge device 30 is preferably in the form of a Wheatstone bridge circuit, as schematically represented in FIG. 6, basically having four electrical contact points connected linearly with one another through four intervening resistors. Specifically, the Wheatstone bridge circuit of the strain gauge device 30 includes a pair of resistors 32,34 mounted to the upper face of the main body 26 and a like pair of resistors 36,38 mounted to the lower face of the main body 26. The four resistors 32,34,36,38 are electrically connected in series with a pair of positive and negative excitation contacts 40,42, respectively, and alternately intervening positive and negative signaling contacts 44,46, respectively. The excitation and signal contacts 40,42,44,46, are connected to respective electrical leads 48,50,52,54, which extend through the cable 15 connecting the two housings 12,14, as more fully explained below.

Figure 2A:
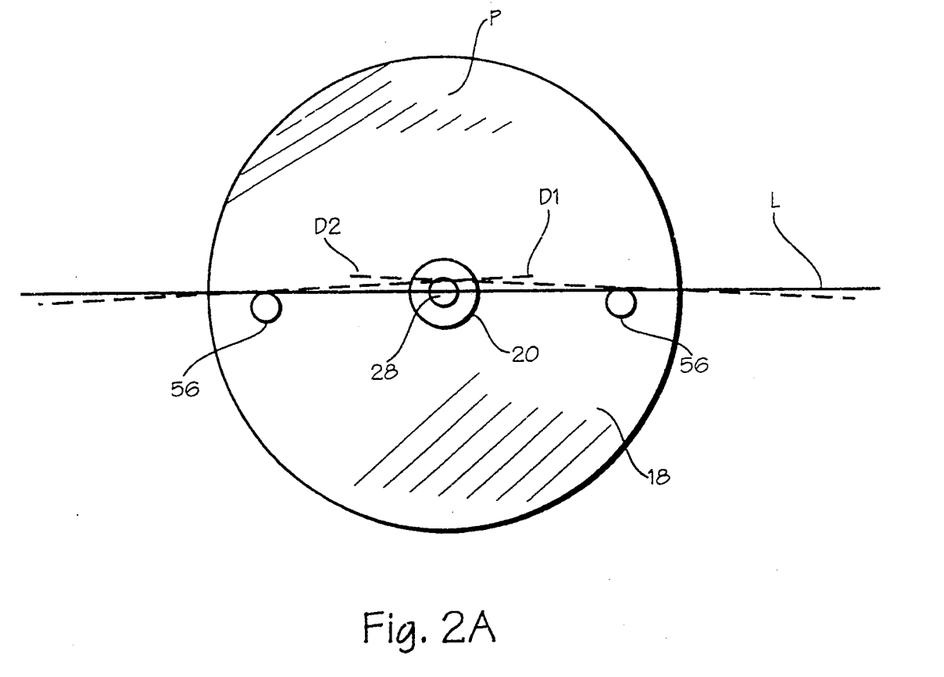
FIGS. 2A and 2B are front elevational views of the first hand-held housing of the apparatus of FIG. 1, showing the fixed contact arms and the sensing arm.
Figure 3:
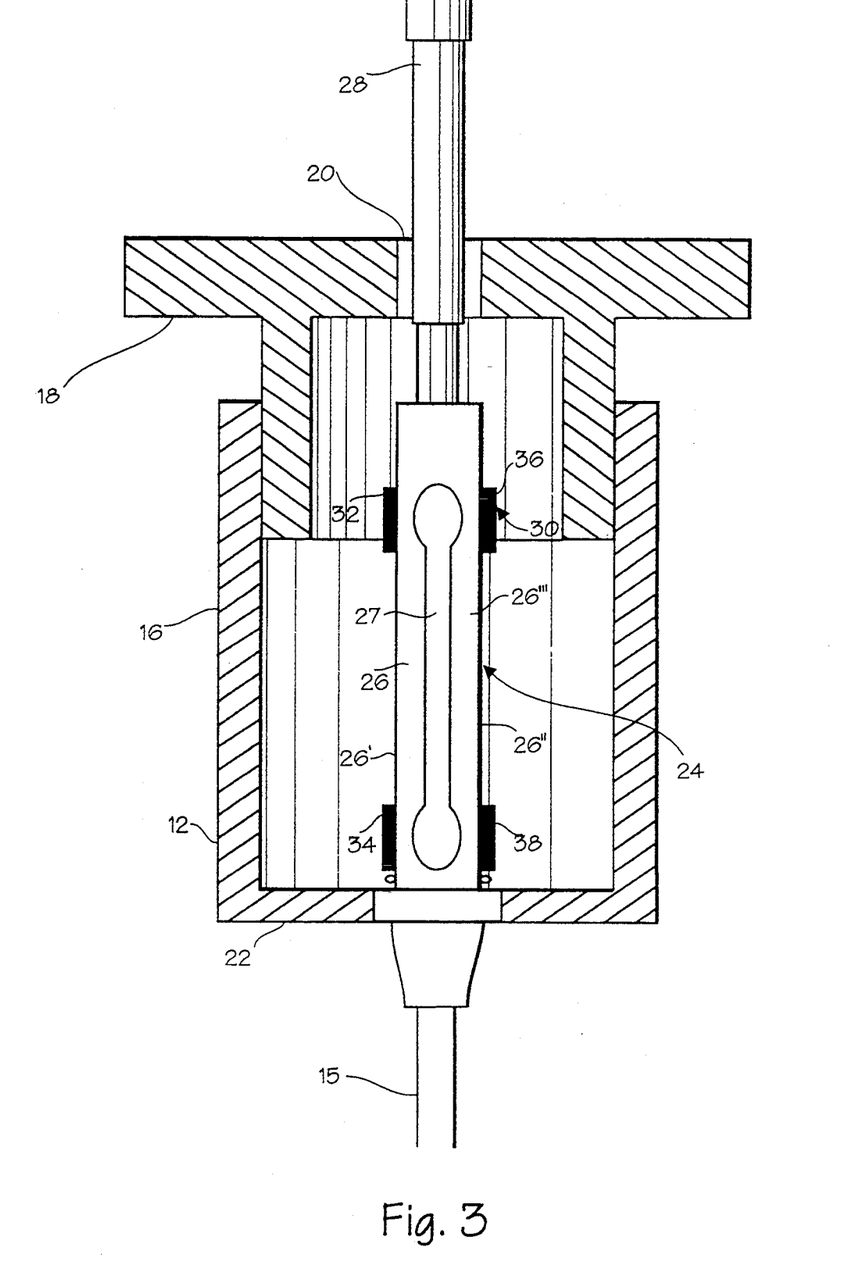
FIG. 3 is a vertical cross-sectional view through the hand-held housing of FIG. 2, taken along line 3—3 of FIG. 1, showing the sensing arm and depicting the strain gauge device schematically.
Figure 4:
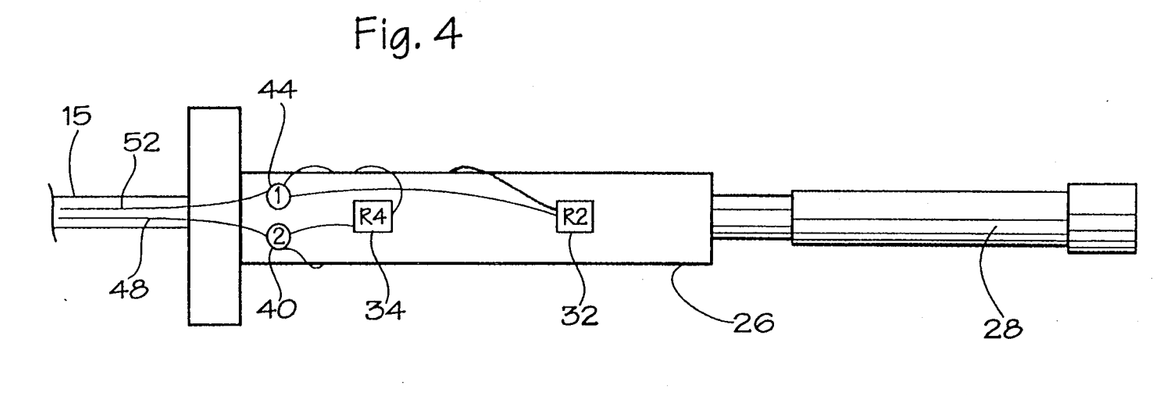
FIG. 4 is a top plan view of the sensing arm assembly of the housing of FIG. 3.
Figure 5:
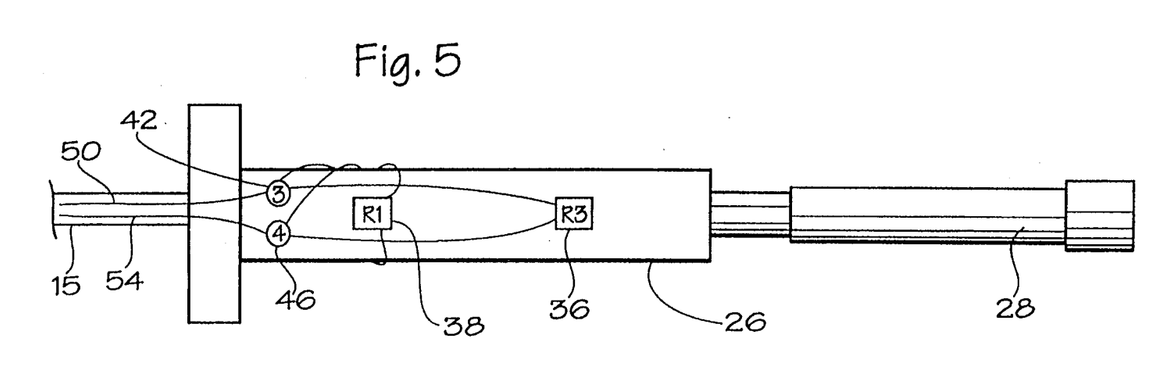
FIG. 5 is a bottom plan view of the sensing arm assembly of the housing of FIG. 3.

A pair of strand contact arms 56 are affixed to and extend outwardly from the circular disk 18 of the cylindrical shell 16 at opposite lateral sides of the deflection plane P and at equal spacings therefrom, as best seen in FIG. 2. In this manner, an imaginary strand contact line L extending tangentially to the strand contact arms 56 is perpendicular to the deflection plane P. The strand contact line L between the strand contact arms 56, however, does not align tangentially with the strand sensing arm 28 but rather is offset a predetermined spacing therefrom. Thus, imaginary strand deflection lines D1, D2 extending, respectively, in tangential relation to the strand contact arms 56 and to the strand sensing arm 28 define equivalent strand break angles with the strand contact line L, which accomplishes purposes more fully described hereinafter.

As best seen schematically in FIG. 6, the housing 14 contains an electrical power supply 58, preferably in the form of a conventional battery which is connected through a microprocessor 60 and through a series of electrical filters, shown only schematically at 62, to provide operational electrical power to the microprocessor 60 and, in turn, to the Wheatstone bridge circuit of the strain gauge device 30. Specifically, the excitation leads 48,50 and the signaling leads 52,54 to the excitation and signaling contacts 40,42,44,46 of the strain gauge device 30 are connected through the filters 62 with the microprocessor 60, whereby the microprocessor 60 controls delivery of positive and negative excitation electrical currents to the contacts 40,42 and receives respective positive and negative signals back from the Wheatstone bridge circuit from the contacts 44,46. The housing 14 additionally supports at the front face of the housing an input pad 64 and a digital display device 66, each connected internally to the microprocessor 60.

The microprocessor has an electronic memory in which a predetermined operational program is stored to continuously compute a quantitative tension value, typically a numeric value in a conventional system of measuring tension, e.g., for determining textile yarn tension in grams of force, based upon the positive and/or negative signals generated by the Wheatstone bridge circuit of the strain gauge device 10 received therefrom through the leads 52,54, according to a conventional predetermined tension measurement formula. Of course, those persons skilled in the art will readily recognize and understand that the microprocessor 60 can be additionally programmed to perform various other calculations, computations and operations.

The input pad 64 is of the conventional type adapted for manual operation by the touch of a user to determine by differing available keystrokes differing modes of operation of the microprocessor 60 according to the operational program stored therein. For example, the input pad may be equipped with an on/off key for connecting and disconnecting the battery 58 with the microprocessor 60, a "tare" key or button for clearing the microprocessor and the bridge circuit to a "zero" starting setting prior to imposing any deflection on the moment arm assembly 24 in a given orientation thereof. Other keys or buttons may be provided to elect alternative processing routines within the microprocessor 60 to calculate tension values to differing increments of measurement and thereby to differing degrees of sensitivity. Another key or button may be provided to control the frequency at which the microprocessor repeats and updates its tension calculations. Another key or button may be provided to instruct the microprocessor to store a particular calculated tension value, e.g. the "peak", ie., maximum, value determined during any given measuring operation.

Figure 2B:
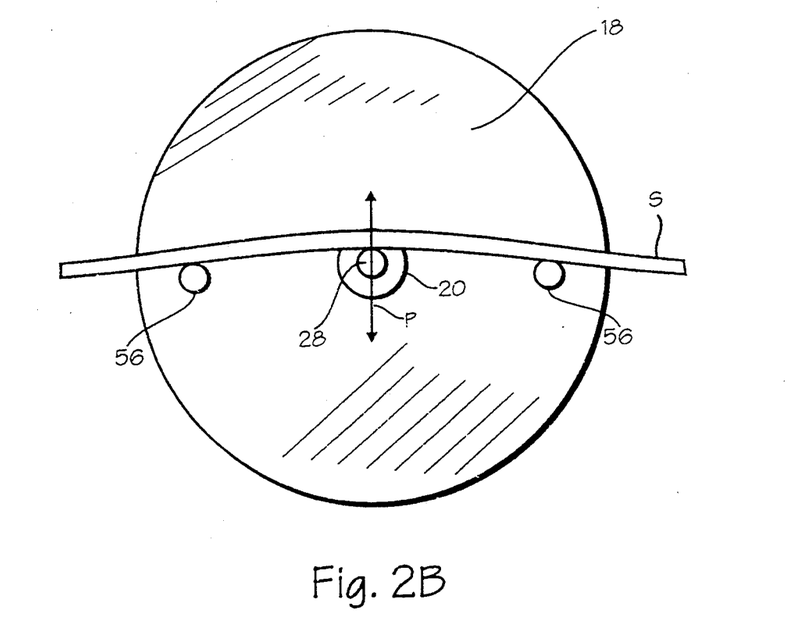

In accordance with the present invention, the apparatus 10 is operated at any given strand tension-measuring location basically by placing the strand contact arms 56 and the strand sensing arm 28 gently in surface contact with a strand whose tension is to be measured. In contrast to conventional wisdom which would typically provide for a sinuous threading of the strand alternately over and under the arms 28,56 in sequence, the present invention contemplates that the arms 28,56 are each to be placed simultaneously in contact with the same common lateral side of the strand, as depicted in FIG. 2B. In this manner, the strand S is caused by the strand sensing arm 28 to deflect from the strand contact line L along which the strand S would otherwise extend between the strand contact arms 56 in the absence of the strand sensing arm 28, the deflection of the strand being at equivalent strand break angles represented by the deflection lines D1,D2. Tension prevailing in the strand S thereby causes a proportional deflection of the moment arm assembly 24 which, under the principles of operation of a Wheatstone bridge circuit, produces a proportional change in the current of the output signal produced at the contacts 44,46. The corresponding signal leads 52,54 transmit such signal changes instantaneously to the microprocessor 60 which, in the ongoing operation of its stored program, continuously computes instantaneously the numeric value of the prevailing strand tension.

In normal operation, the user will initially perform a "tare" routine with the apparatus 10 before each strand tension measurement is taken, by orienting the housing 12 to dispose the strand sensing and contact arms 28,56 in the appropriate horizontal/vertical disposition necessary to be placed in simultaneous contact with the particular strand S to be measured, but without yet contacting the arms 28,56 with the strand. The corresponding "tare" routine stored in the microprocessor recognizes the orientation of the housing 12 and stores the signal values being received from the leads 52,54 as a starting "zero" setting representing no tension-imposed deflection of the moment arm assembly 24. This operation is significant and important because the strain gauge 30 of the moment arm assembly 24 is sufficiently sensitive to detect its own mass.

With the microprocessor 60 thusly prepared for a given measurement, the housing 12 is held by the user in the same orientation and moved to place the sensing and contact arms 28,56 in gentle simultaneous contact with the strand to be measured, whereupon the resultant deflection of the moment arm assembly 24 produces a proportional change in the electrical signal to the microprocessor 60 through the leads 52,54 and the microprocessor correspondingly computes a tension value. The tension value is displayed on the digital display device 66, which changes as the tension computation is updated by the microprocessor 60, until the measurement operation is terminated. At that point, the user can store the peak tension value through an appropriate key stroke on the input pad 64. Advantageously, the moment arm assembly 24 of the present invention is sufficiently sensitive to determine tension fluctuations as small as 0.1 grams, making the present apparatus uniquely suited for measuring low levels of tension in applications such as textile applications wherein fragile microdenier filaments and spandex yarns are being handled, in the handling of fiberoptic strands, etc.

It will therefore be readily understood by those persons skilled in the art that the present invention is susceptible of broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

We claim:

1. Apparatus for measuring prevailing instantaneous tension in an elongate strand comprising a pair of fixed contact elements arranged at a spacing from one another, the fixed contact elements defining a strand contact line therebetween for simultaneously contacting the strand in-situ at a common lateral side thereof at respective points along the strand contact line, a sensing element supported in a deflectable cantilevered disposition intermediate the fixed contact at an equal spacing from each thereof and at a lateral spacing from the strand contact line for contacting the strand simultaneously with the fixed contact elements at a sensing point at the same common lateral side of the strand to cause the strand to deflect from the strand contact line at equivalent strand break angles between the respective strand contact points on the fixed contact elements and the sensing point on the sensing element, the sensing element having an opening laterally therethrough for reducing the force required to deflect the sensing element from a resting cantilevered position, the opening being of an ellipsoidal shape in relation to the length of the sensing element, and electrically powered strain gauge means associated with the sensing element for generating a continuous electrical output signal varying instantaneously in proportion to the corresponding instantaneous tension prevailing in the strand in contact with the fixed contact elements and the sensing element.

2. Apparatus for measuring prevailing instantaneous tension in an elongate strand according to claim 1, wherein the strain gauge means comprises a Wheatstone bridge circuit having excitation means and signal means at each of two opposite sides of the sensing element relative to a plane of deflection normal to the strand contact line for producing the electrical output signal in proportion to both strand tension increases and decreases.

3. Apparatus for measuring prevailing instantaneous tension in an elongate strand according to claim 1, further comprising a housing, the fixed contact elements, the sensing element and the strain gauge means being mounted to the housing.

4. Apparatus for measuring prevailing instantaneous tension in an elongate strand according to claim 3, wherein the housing is configured to be held in a user's hand for portability.

5. Apparatus for measuring prevailing instantaneous tension in an elongate strand according to claim 1, further comprising means for computing a quantitative tension value from the output signal of the strain gauge means.

6. Apparatus for measuring prevailing instantaneous tension in an elongate strand according to claim 5, further comprising means for displaying the tension value computed by the computing means.

7. Apparatus for measuring prevailing instantaneous tension in an elongate strand according to claim 6, wherein the computing means continuously computes the tension value instantaneously from the output signal and the display means continuously displays the instantaneously computed tension value.

8. Apparatus for measuring prevailing instantaneous tension in an elongate strand according to claim 7, further comprising an electrical power supply source connected to the strain gauge means, the computing means and the display means.

9. Apparatus for measuring prevailing instantaneous tension in an elongate strand according to claim 8, further comprising portable housing means to be carried in a user's hands from one strand tension-sensing location to another, the fixed contact elements, the sensing element, the strain gauge means, the computing means, the display means and the electrical supply source being mounted to said housing means.

10. Apparatus for measuring prevailing instantaneous tension in an elongate strand according to claim 9, wherein the housing means comprises a first portable housing to be held in one hand of a user and a second portable housing to be held in the other hand of the user, the fixed contact elements, the sensing element and the strain gauge means being mounted to the first housing and the electrical supply source, the computing means and the display means being mounted to the second housing, electrical lead means extending between the first and second housings for connecting the strain gauge means with the electrical supply source, the computing means and the display means.

11. Apparatus for measuring prevailing instantaneous tension in an elongate strand according to claim 1, wherein the fixed contact elements comprise fixed contact arms and the sensing element comprises a sensing arm.

12. Apparatus for measuring prevailing instantaneous tension in an elongate strand comprising a sensing arm supported in a deflectable cantilevered disposition for contacting the strand to cause the strand to deflect about the sensing arm, the sensing arm having an opening laterally therethrough for reducing the force required to deflect the sensing arm from a resting cantilevered position, the opening being of an ellipsoidal shape in relation to the length of the sensing arm, and electrically powered strain gauge means associated with the sensing arm for generating a continuous electrical output signal varying instantaneously in proportion to the corresponding instantaneous tension prevailing in the strand in contact with the sensing arm.

13. Apparatus for measuring prevailing instantaneous tension in an elongate strand according to claim 12, wherein the strain gauge means comprises a Wheatstone bridge circuit having excitation means and signal means at each of two opposite sides of the sensing arm relative to a plane of deflection normal to a line of strand contact with the sensing arm for producing the electrical output signal in proportion to both strand tension increases and decreases.

14. Apparatus for measuring prevailing instantaneous tension in an elongate strand according to claim 12, further comprising a housing, the sensing arm and the strain gauge means being mounted to the housing.

15. Apparatus for measuring prevailing instantaneous tension in an elongate strand according to claim 14, wherein the housing is configured to be held in a user's hand for portability.

16. Apparatus for measuring prevailing instantaneous tension in an elongate strand according to claim 12, further comprising means for computing a quantitative tension value from the output signal of the strain gauge means.

17. Apparatus for measuring prevailing instantaneous tension in an elongate strand according to claim 16, further comprising means for displaying the tension value computed by the computing means.

18. Apparatus for measuring prevailing instantaneous tension in an elongate strand according to claim 17, wherein the computing means continuously computes the tension value instantaneously from the output signal and the display means continuously displays the instantaneously computed tension valve.

19. Apparatus for measuring prevailing instantaneous tension in an elongate strand according to claim 18, further comprising an electrical power supply source connected to the strain gauge means, the computing means and tile display means.

20. Apparatus for measuring prevailing instantaneous tension in an elongate strand according to claim 19, further comprising portable housing means to be carried in a user's hands from one strand tension-sensing location to another, the sensing arm, the strain gauge means, the computing means, the display means and the electrical supply source being mounted to said housing means.

21. Apparatus for measuring prevailing instantaneous tension in an elongate strand according to claim 20, wherein the housing means comprises a first portable housing to be held in one hand of a user and a second portable housing to be held in the other hand of the user, the sensing arm and the strain gauge means being mounted to the first housing and tile electrical supply source, the computing means and the display means being mounted to the second housing, electrical lead means extending between the first and second housings for connecting the strain gauge means with the electrical supply source, the computing means and the display means.

22. Apparatus for measuring prevailing instantaneous tension in an elongate strand comprising a pair of fixed contact arms arranged at a spacing from one another, the fixed contact arms defining a strand contact line therebetween for simultaneously contacting the strand in-situ at a common lateral side thereof at respective points along the strand contact line, a sensing arm supported in a deflectable cantilevered disposition intermediate the fixed contact arms at an equal spacing from each thereof and at a lateral spacing from the strand contact line for contacting the strand simultaneously with the fixed contact arms at a sensing point at the same common lateral side of the strand to cause the strand to deflect from the strand contact line at equivalent strand break angles between the respective strand contact points on the fixed contact arms and the sensing point on the sensing arm, electrically powered strain gauge means associated with the sensing arm for generating a continuous electrical output: signal varying instantaneously in proportion to the corresponding instantaneous tension prevailing in the strand in contact with the fixed contact arms and the sensing arm, means for continuously computing a quantitative tension value instantaneously from the output signal of the strain gauge means, means for continuously displaying the tension value instantaneously computed by the computing means, an electrical power supply source connected to the strain gauge means, the computing means and the display means, portable housing means to be carried in a user's hands from one strand tension-sensing location to another, the housing means comprising a first portable housing to be held in one hand of a user and a second portable housing to be held in the other hand of the user, the fixed contact arms, the sensing arm and the strain gauge means being mounted to the first housing and the electrical supply source, the computing means and the display means being mounted to the second housing, and electrical lead means extending between the first and second housings for connecting the strain gauge means with the electrical supply source, the computing means and the display means.

* * * * *

UNITED STATES PATENT AND TRADEMARK OFFICE
CERTIFICATE OF CORRECTION

PATENT NO. : 5,433,116

DATED : July 18, 1995

INVENTOR(S) : Kevin S. Ahlstrom and Thomas Bartlett

Page 1 of 2

It is certified that error appears in the above-identified patent and that said Letters Patent is hereby corrected as shown below:

Abstract, line 9 (not including heading), delete "stand" and insert therefor -- strand --.

Column 1, line 46, delete "objection" and insert therefor -- object --.

Column 3, line 34, after "14" delete ",".

Column 3, line 48, delete "parallelpiped" and insert therefor -- parallelepiped --.

Column 3, line 55, delete "parallelpiped" and insert therefor -- parallelepiped --.

Column 3, line 65, delete "26''" and insert therefor -- 26''' --.

Column 4, line 20, after "46" delete ",".

Column 4, line 67, delete "strain gauge device 10" and insert therefor -- strain gauge device 30 --.

Column 5, line 26, delete "ie." and insert therefor -- i.e. --.

Column 6, line 25, delete "fiberoptic" and insert therefor -- fiber optic --.

Column 6, line 56, after "contact" insert -- elements --.

Column 8, line 48, delete "valve" and insert therefor -- value --.

Column 8, line 53, delete "tile" and insert therefor -- the --.

UNITED STATES PATENT AND TRADEMARK OFFICE
CERTIFICATE OF CORRECTION

PATENT NO. : 5,433,116

DATED : July 18, 1995

INVENTOR(S) : Kevin S. Ahlstrom and Thomas Bartlett

It is certified that error appears in the above-identified patent and that said Letters Patent is hereby corrected as shown below:

Column 8, line 68, delete "tile" and insert therefor -- the --.

Column 10, line 1, after "output" delete ":".

Signed and Sealed this

Twenty-third Day of July, 1996

Attest:

BRUCE LEHMAN

Attesting Officer

Commissioner of Patents and Trademarks